United States Patent [19]
Henley et al.

[11] Patent Number: 6,027,712
[45] Date of Patent: *Feb. 22, 2000

[54] IMMUNOTHERAPY OF INFLAMMATORY SINUS AND EAR DISEASE

[76] Inventors: Julian L. Henley, 38 Munger Rd., Guilford, Conn. 06437; Adrienne A. Denese, 31 E. 63rd St., New York, N.Y. 10021

[*] Notice: This patent issued on a continued prosecution application filed under 37 CFR 1.53(d), and is subject to the twenty year patent term provisions of 35 U.S.C. 154(a)(2).

[21] Appl. No.: 08/677,778

[22] Filed: Jul. 10, 1996

Related U.S. Application Data

[63] Continuation of application No. 08/177,162, Jan. 4, 1994, abandoned.

[51] Int. Cl.[7] ........................................... A61K 9/12
[52] U.S. Cl. ............................ 424/45; 514/2; 514/871; 514/887
[58] Field of Search ............................. 424/45; 514/887, 514/2, 871

[56] References Cited

U.S. PATENT DOCUMENTS 5,075,222  12/1991  Hannum et al. ........................ 435/69.1

OTHER PUBLICATIONS

Evans, C. H., and P. D. Robbins. (1994). Receptor, vol. 4, p. 9–15.

*Primary Examiner*—Raj Bawa
*Attorney, Agent, or Firm*—Michael G. Petit

[57] ABSTRACT

A composition and method useful for treating commonly occurring inflammatory disease of the nose, ears and sinuses are described. Interleukin-1 (IL-1), a naturally occuring and generally non-toxic composition, is one of the key mediators of the biomolecular inflammatory reaction. IL-1 antagonists have been found in the human body. The IL-1 antagonists are thought to function as natural modulators of the inflammatory response. The present invention employs IL-1 receptor antagonist to block the runaway inflammatory cascade associated with inflammatory disease of the paranasal sinuses and middle ear. The composition and method prevents the long term complications of this disease and reduces the need for costly surgical intervention which is currently performed in more advanced cases.

1 Claim, 3 Drawing Sheets

IL-1 RECEPTOR ANTAGONIST ACTION

IL-1 RECEPTOR BLOCKED FROM IL-1 STIMULATION

IMMUNOTHERAPY OF INFLAMMATORY SINUS AND EAR DISEASE

CROSS-REFERENCE TO RELATED APPLICATIONS

This is a continuation of application Ser. No. 08/177,162; filed Jan. 04, 1994 now abandoned.

BACKGROUND OF INVENTION

1. Field of the Invention

The invention provides a method and composition for treating inflammatory disease and more particularly a composition and method for treating inflammatory disease of the nose, paranasal sinuses and ears.

2. Prior Art

Inflammatory disease of the paranasal sinuses is a common disorder afflicting many people. It is characterized by repeated episodes of inflammation, precipitated initially by environmental factors such as smoke, pollutants or allergens, and often followed by a secondary bacterial infection. Exposure to such environmental inhalants stimulates the first stage of an edematous swelling of the membranes of the nose and a partial blockage of sinus drainage. The stroma becomes hyperemic, edematous and infiltrated with neutrophils, lymphocytes, and plasma cells. Serous and mucinous fluid exudes though the epithelium. Clinically these changes manifest as nasal stuffiness and rhinorrhea. If bacterial infection is superimposed, neutrophils dominate the inflammatory infiltrates that become evident as a thick purulent discharge.

Similar reactions to allergens and infectious agents occur in the mucosa of the paranasal sinuses and readily occlude the sinus ostia (openings). Superimposed bacterial infections of the occluded sinuses are referred to as sinusitis and can lead to serious complications depending on the location of the sinus. Ethmoidal air cell infection may spread into the orbital soft tissue and the meninges. Frontal sinusitis can result in meningitis and osteomyelitis of the frontal bone. Sphenoiditis may lead to retrobulbar neuritis and cavernous sinus thrombosis. The current treatment of this disorder involves a combination of the use of antibiotics, both systemic and topical anti-inflammatory agents and decongestants. More recently topical steroid sprays have been introduced as well as cromolyn which intervenes in this inflammatory process and produces clinical improvement in some of these patients. Unfortunately, many of these patients continue to have advancing disease that leads to total obstruction and a chronic sinusitis. These patients ultimately undergo surgical intervention. The classical surgical techniques involve radical exoneration of polypoid tissue from the nose and paranasal sinuses and the establishment of proper drainage. Such surgery is performed in the hospital under general anesthesia where a fair amount of bleeding is encountered along with some morbidity, not to mention the surgical risks of ocular and intracranial complications of such an extensive sinus surgery.

The presence of the inflammatory process in the nasal and paranasal mucosa often gives rise to polyp formation. Persistence of these inflammatory changes leads to infiltration by neutrophils, lymphocytes and eosinophiles. These inflammatory sequence of events have been well described in the medical literature and many cells have been implicated in this inflammatory process. It is well known from descriptive pathology that the inflammatory and hyperplastic phase is characterized by following stages:

I. edematous stage,
II. granular or infiltrating stage,
III. fibrous stage,
IV. mixture of any of these stages;
V. chronic inflammation with exudation.

The usual sequence of pathological events is that the submucous tissue is infiltrated with serum and leukocytes fill the voids within the mesh (stage I). The capillaries become dilated and the mucous membrane is greatly thickened and erythematous (stage II). The result of this edema is the engorgement of the subepithelial structures. In stage III the serum and leukocytes escape through the epithelial covering of the mucosa where they become mixed with bacteria and epithelial debris as well as mucous. These secretions, initially thin, later become thicker and more viscous. Some of the fibrin from the serum transudates. Stage IV is usually characterized by the resolution and the absorption of the exudate. Unfortunately stage five often results, in which the inflammatory process progresses from the congestive to the purulent type. During stage V, the leukocytes are being shed in immense numbers. At this stage the tissue changes become permanent with increasing fibrosis and a chronic condition is established. Because of the increasing blockage, phlebitis of the perforating veins and blockage of the drainage of the sinuses occurs.

Recent advances in surgical techniques have produced such tools as Hopkins lenses and endoscopic equipment suitable for the visualization of the osteo meatal complex of the sinuses. These instruments and techniques have reduced some of the complexity of the surgery and improved intranasal visualization during surgery. Unfortunately, the continued costs of management have remained high and surgical intervention and physical removal of polyps has not offered a cure for, or the resolution of the underlying disease. These polyps have the tendency to recur in spite of extensive and even radical sinus surgery.

There are numerous medical classifications of chronic inflammatory ear disease. The middle ear cleft is connected to the nasopharynx by means of an elongated ostium referred to as the Eustachian tube. The ear is subject to frequent inflammatory illnesses beginning in childhood. Serous otitis media of childhood is quite frequent as well as acute otitis media. These two conditions alone probably account for the majority of visits to the pediatric doctor's office and may constitute the key market for pediatric antibiotics. These early disorders frequently lead to more chronic conditions such as secretory-adhesive otitis media and chronic otitis media. These more advanced conditions often require surgical intervention in the form of draining the ears surgically and placing tubes in the tympanic membrane for longer term middle ear cleft drainage and ventilation. This procedure is one of the most commonly performed operations in the US. This represents significant monetary costs to society as well as occasional anesthesia morbidity given the frequency of the procedure. The clinical etiology of chronic otitis media is almost identical to that of chronic sinusitis where allergic, environmental, viral, and microbial factors have been implicated. Anatomically the middle ear, mastoid air cells, and the Eustachian tube complex and the ciliary mucosal lining bear remarkable relationship to other paranasal sinuses described above. The pathophysiology as well as the cellular immunology of chronic otitis media is similar to chronic sinusitis if not one of the same. It is the contention of the present inventors that the method of treating chronic inflammatory sinusitis described herein also applies to the treatment of chronic otitis media.

CELLULAR-MOLECULE EVENTS IN CHRONIC SINUSITIS

Researchers are currently isolating and identifying the chemotactic agents that stimulate the release of histamines, leukotrienes and peptide factors which orchestrate the complex mechanism of an immunological and inflammatory response. Unfortunately, in most situations, where patient experiences clinical sinus and nasal problems, the inflammatory process has gone out of control and the persistent inflammatory tissue that ultimately leads to growth of nasal polyps, now begins to entrap bacteria and prevent proper drainage of paranasal sinuses.

The sequence of events in the inflammatory process is outlined in FIG. 1. The complement-mediated acute inflammatory reaction has two central pathways: the mast cell-mediated pathway indicated at the letter A on the right had side of FIG. 1 and the macrophage-mediated pathway indicated at B. Both pathways A and B respond to complement stimulation (not shown) and they mutually reinforce each other providing an example of a fail-safe redundancy system. The defensive scenario is initiated by the alternative complement pathway. As a first step C3 (not shown) is fragmented into C3a and C3b (not shown). The C3b fragment (not shown) copiously coats the surface of an invading microbe (not shown) through a process known as opsonization, whereas the C3a activates the next step in the sequence and generates C5a. C5a is a potent neutrophil chemotactic agent and has a striking ability to act directly on the capillary endothelium to produce vasodilatation and increase capillary permeability. This effect is prolonged by leukotriene B4 released by activated mast cells, neutrophils, and macrophages. The mast cell, in response to C3a and C5a, produces a number of mediators shown in FIG. 1 which ultimately act to recruit polymorphonuclear neutrophils and further plasma complement components to the site of the microbial invasion. In general these mediators such as, for example, histamine, leukotriene B4 and prostaglandins, induce vasodilatation, increased capillary permeability and provides chemotactic stimuli for neutrophils to migrate into the site of inflammations.

As noted earlier, tissue macrophages may mediate a parallel series of events as shown in pathway B with the same final result via the key step of manufacturing IL-1 and Tumor Necrosis Factor (BNF) (not shown). Bacterial toxins, yeast, viruses, immune complexes, environmental irritants, the presence of C3b opsonized microbes and/or the direct action of C5a stimulates the macrophage to produce the mediators of an acute inflammatory response. Of these, IL-1 along with the TNF is of key importance. IL-1 induces adhesion molecules for neutrophiles on the surface of endothelial cells and promote the secretion of a neutrophil activation peptide. Under the influence of chemotaxis produced by IL-1, neutrophils slow down, marginate under the influence of the surface adhesion molecules and pass through the gaps between the endothelial cells. The neutrophils then move to the site of microbial invasion and consume the C3b coated microbes. IL-1 produces a potent neutrophil chemotactic factor known as IL-8 which draws neutrophiles to the site of inflammation. Furthermore, during an infectious process, IL-1 produces Acute Phase Proteins that have a key role in the organization of the second mechanism of defense, namely the Humoral Mechanism of defense. The macrophage also induces the production of PGE2 (not shown) and Leukotriene B4 both of which increase vascular permeability thereby supporting the IL-1 effect of neutrophil movement into the interstitium. IL-1 also induces T cell activation via the induction of IL-2 production and induces the proliferation of B cells and stimulates antibody production all of which further augment the immune response.

The above outlined inflammatory response, while it is essential for the basic body defense mechanisms, is the cause of multiple pathological conditions when it becomes uncontrolled. While the resulting pathologies are wide ranging including rheumatoid arthritis, osteoarthritis, and other autoimmune diseases, it is helpful and exemplary to focus attention on the development of chronic sinusitis and polyp formation as a manifestation of a magnified and out of control form of the inflammatory response. Current clinical efforts to counteract the uncontrolled inflammatory response focus on histamine blockers, and topical steroids. Histamine blockers may decrease vasodilatation, capillary permeability and chemotaxis but, as is apparent from FIG. 1, there are other substances besides histamine that subserve the same function thus rendering histamine blockers only partially effective. The Nonsteroidal Anti inflammatory (NSAID) medications provide blockage at various points of the Arachidonic pathway (shown in part in pathway A) blocking Leukotriene, prostaglandins and thromboxanes. The function of the above substances is also somewhat redundant therefore blockage of one or the other may only serve as a partial blockage of the particular function. Steroid administration is the most effective among the above mentioned clinical approaches in the control of chronic inflammatory disease. Systemically and locally administered steroid treatment is the current mainstay of the non surgical management of inflammatory ear and sinus disease once the offending microbial entities have been eradicated. Although the clinical experience with steroid administration is extensive, its effect on the inflammatory response is limited and its systemic use is curtailed by significant and deleterious side effects. The IL-1 pathway inhibition by the method of treatment described herein offers a significant improvement in the control and management of inflammatory sinus and ear disease without deleterious side effects. The present invention provides a new modality of treatment for this common and refractory disease of the ears, nose and paranasal sinuses.

In U.S. Pat. No. 5,075,222, the contents of which are incorporated herein by reference, Hannum et al. disclose specific DNA sequences which encode for Interleukin-1 inhibitors. Such sequences can be employed to produce Interleukin-1 inhibitors via recombinant DNA techniques. In addition to disclosing the amino acid sequence of Interleukin-1 inhibitors, the author's further disclose a secretory "leader" amino acid sequence which permits the secretion of the Interleukin-1 inhibitor by the cell subsequent to intracellular translation which facilitates separation and purification of the secreted Interleukin-1 inhibitor from a cell-free extract.

> Interleukin-1 has been identified and implicated as a mediator of inflammatory arthritis, lupus erythematosus, and lung disease (*Interleukin-1, Inflammation and Disease,* eds. R. Bomford and B. Henderson, Elsevier, 1989). Hannum et al. (i.b.i.d.) suggest the use of Interleukin-1 inhibitors for controlling these conditions. Therapeutic agents blocking the action of Interleukin-1 may be active at many different levels including synthesis, Interleukin-1 secretion or the ability of the target cell receptors to bind to the Interleukin-1 (a protein). Hannum et al. disclose a process for purifying three macrophage-derived Interleukin-1 inhibitors. In view of the interest in Interleukin-1 inhibitors for treating systemic inflammatory conditions, it is surprising that employing Interleukin-1 inhibitors for treating chronic inflammation of the sinus, nose and/or ears has been neither suggested nor attempted.

SUMMARY OF THE INVENTION

The present invention utilizes the sequence of the chemical factors that hasten the uncontrolled inflammatory response as a means for intervening in this uncontrolled inflammatory response. In the case of sinusitis, the disease extends into the walls of the paranasal sinuses. This well established pathological description, although microvisual in nature and descriptive of the cells involved, can also be explained by the sequence of events at the molecular level when the interleukin pathway is implicated.

It is another object of this invention to provide a composition useful for treating inflammatory disease of the nose and paranasal sinuses.

It is an object of this invention to provide a composition for treating nasal polyps.

It is still another object of the invention to provide a method for treating inflammatory disease of the ear.

It is yet another object of the invention to provide a method and composition for treating inflammatory disease of the nose and paranasal sinuses.

Although any of the naturally occurring IL-1 antagonists or suppressants can be used to expedite the method of treatment described herein it is preferred to use a commercially available source such as Antril® a product of Synergen Corp. Other similar molecules that can function as IL-1 suppressors and/or receptor antagonists can also be used in the method of treatment described in the present invention.

Interleukin-1 (IL-1) is a small polypeptide with a molecular weight of 17.3 kD. The non-glycosylated form of human IL-1ra has been isolated, purified and produced by recombinant DNA technology using *E coli* fermentation and subsequent purification to obtain pharmaceutical grade material. The recombinant form of Il-1ra has 153 amino acids and is identical to the non-glycosylated form of human IL-1ra except for the addition of a N-terminal methionine. The amino acid sequence of the recombinant form of IL-1ra is given below:

```
Met Arg Pro Ser Gly Arg Lys Ser Ser Lys Met Gln Ala Phe Arg Ile Trp Asp Val Asp  20

Gln Lys Thr Phe Tyr Leu Arg Asp Asp Gln Leu Val Ala Gly Tyr Leu Gln Gly Pro Asp  40

Val Asp Leu Glu Glu Lys Ile Asp Val Val Pro Ile Glu Pro His Ala Leu Phe Leu Gly  60

Ile His Gly Gly Lys Met Cys Leu Ser Cys Val Lys Ser Gly Asp Glu Thr Arg Leu Gln  80

Leu Glu Ala Val Asp Ile Thr Asp Leu Ser Glu Asp Arg Lys Gln Asp Lys Arg Phe Ala 100

Phe Ile Arg Ser Asp Ser Gly Pro Thr Thr Ser Phe Glu Ser Ala Ala Cys Pro Gly Trp 120

Phe Leu Cys Thr Ala Met Glu Ala Asp Gln Pro Val Ser Leu Thr Asp Met Pro Asp Glu 140

Gly Val Met Val Thr Lys Phe Tyr Phe Glu Glu Asp Glu                              153;
```

DESCRIPTION OF THE PREFERRED EMBODIMENT

It is well documented that one of the main substances that can decrease IL-1 production is a steroid. IL-1 has a multifaceted and broad spectrum of activity in the induction and maintenance of inflammatory response as compared to the narrower scope of histamine and the factors generated in the arachidonic acid pathway. The present teaching proposes that the effectiveness of steroids in the control of chronic inflammatory response is due, in part, to the suppression of the IL-1 pathway. The use of IL-1 receptor antagonist for treating chronic sinusitis has never before been suggested in the medical literature. Several IL-1 receptor antagonist molecules have been identified. IL-1 receptor antagonist has been isolated from the urine of septic patients, and from human monocytes infected by CMV and HTLV-3/HIV infections. It is possible that the virally induced hypersecretion of IL-1 antagonist causes the associated immunosuppression.

Figure 2:
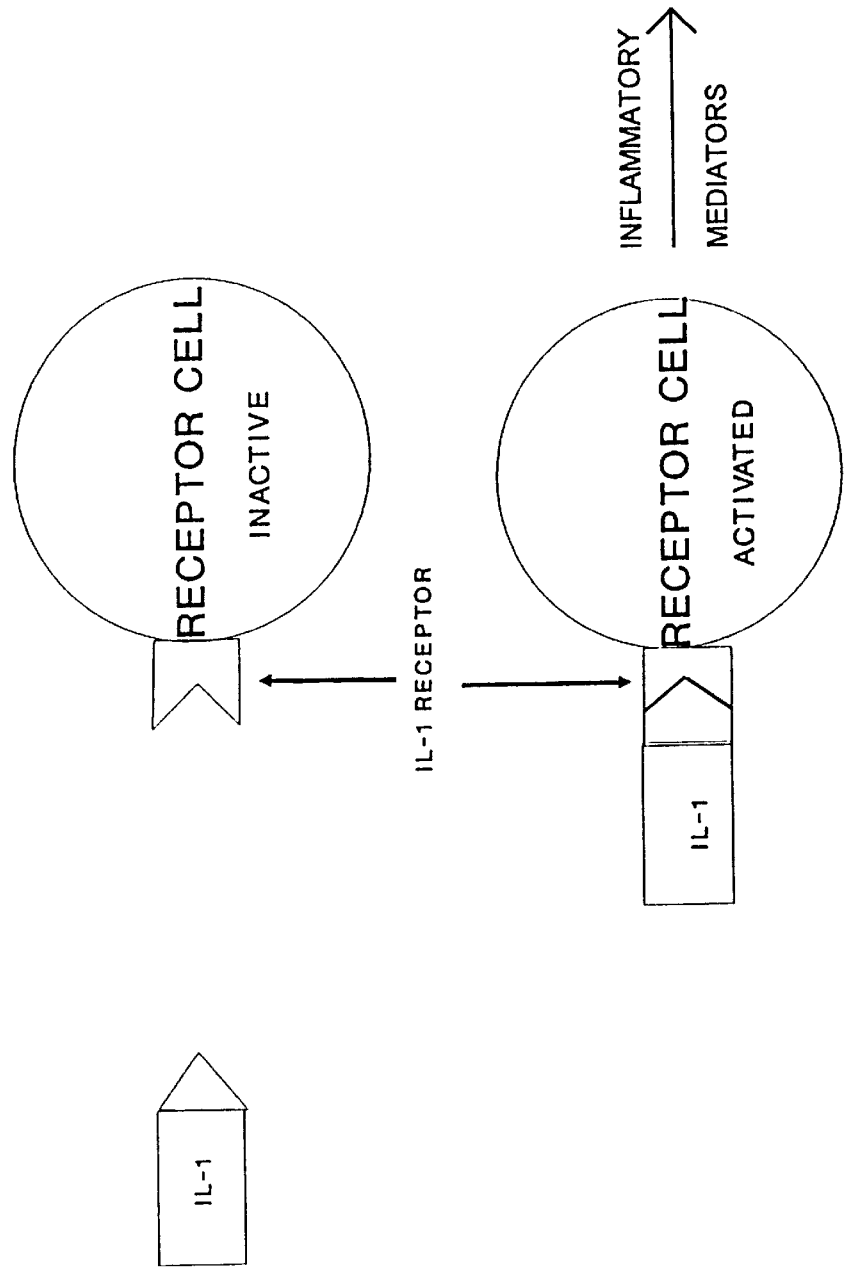
FIG. 2 is a schematic diagram showing Interleukin-1-mediated cell activation.

It exists in two major isoforms; IL-1 Alfa, and IL-1 Beta, and it possesses a wide spectrum of inflammatory, immunologic, metabolic, physiological and hematopoietic properties. Although a variety of cells produce IL-1 including macrophages, keratinocytes, dendritic cells, astrocytes, B and T cells, neutrophils and fibroblasts, the principal producers of IL-1 are the macrophages, fibroblasts and T and B cells. Except for skin keratinocytes, some epithelial cells and certain cell in the CNS; IL-1 production is not observed in the above mentioned principal cell sources in health, only during disease. IL-1 production is triggered by infections, microbial toxins, inflammatory agents and allergic reactions. Overall the chief functions of IL-1 is to regulate the amplitude and duration of the immune response at sites of inflammation or allergic immune reaction. FIG. 2 describes how IL-1 affects target cells.

Figure 1:
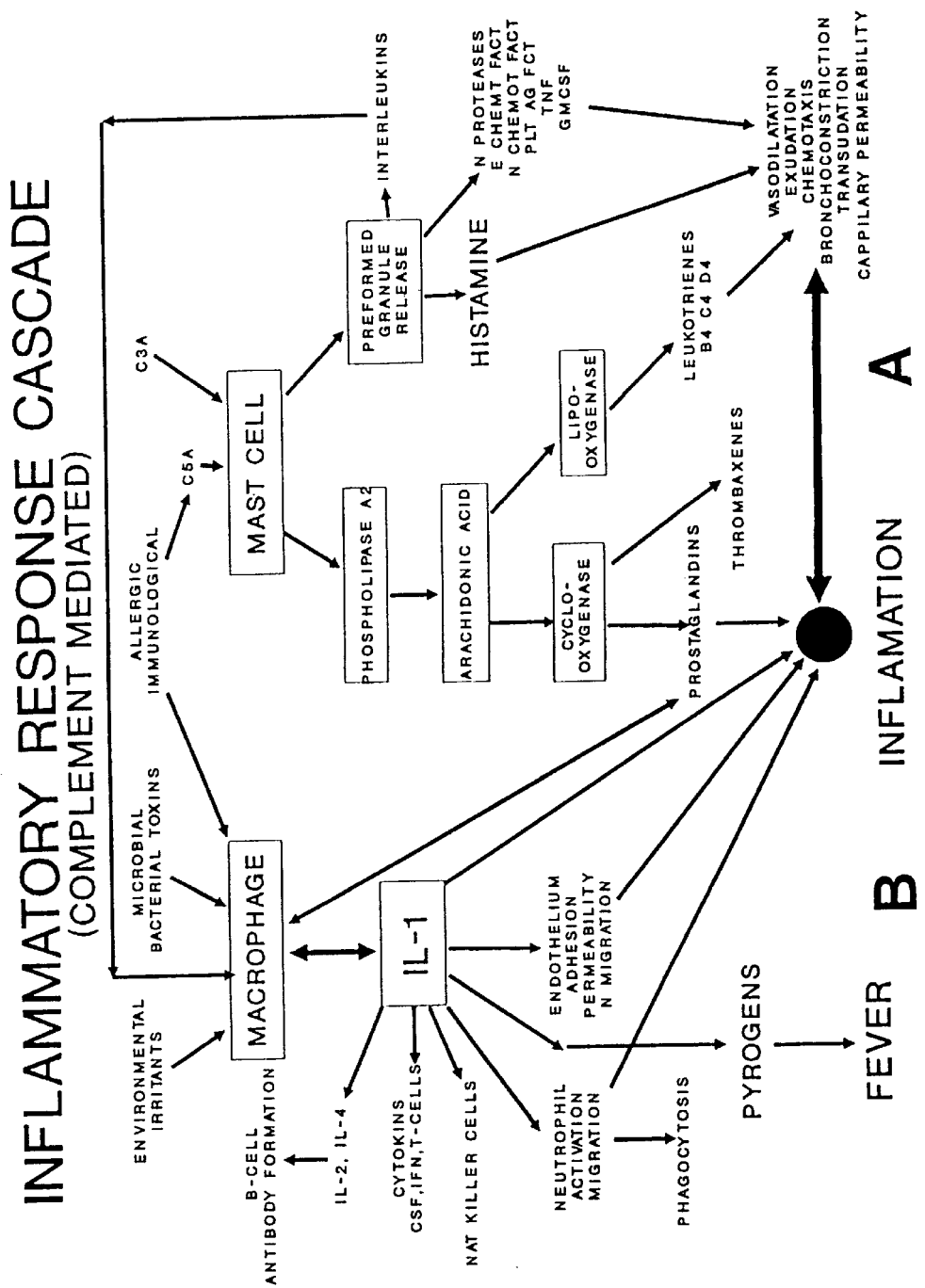
FIG. 1 is a schematic diagram of the Inflammatory Response Cascade.

IL-1 induces macrophages and monocytes (receptor cells) to produce inflammatory mediators such as Prostaglandin E2, IL-6 and the neutrophil attracting peptide IL-8. Furthermore it promotes the proliferation of T lymphocytes by enhancing the production of T Lymphocyte derived lymphokines such as IL-2. It also augments B cell proliferation, surface immunoglobulin receptor expression and antibody production. IL-1 acts as a chemotaxic agent for neutrophils. It also stimulates adhesiveness of neutrophils to endothelial cells thereby inducing neutrophil infiltration into the interstitial inflammatory sites. Pathway B of the Inflammatory Response Cascade shown in FIG. 1 describes IL-1 function on Lymphoid as well as non-lymphoid tissue.

Injection of IL-1 in large quantities induces a local acute inflammatory response that begins within one hour and peaks in 3–4 hours. This cascade of inflammatory events is described by the following steps. Initially neutrophils adhere to endothelial cells and marginate or accumulate along blood vessel walls. This is followed by neutrophil infiltration and edema secondary to extravasation of fluids into the interstitium of the inflammatory site. In contrast, experimentally induced slow release of IL-1 results in delayed type hypersensitivity, granuloma formation with considerable mononuclear cell infiltration, fibrosis and new blood vessel formation that are consistent with the clinical picture of a chronic inflammatory response as observed in chronic sinusitis and polyp formation.

More relevant to chronic sinusitis and polyp formation is the fact IL-1 potentiates the effect of the Epidermal Growth Factor (EGF) and it is one of the most potent activators of fibroblast proliferation by directly increasing the transcription of collagen type I, III, and IV. Certain activities of IL-1 maybe of pathological importance in the development of chronic sinusitis and polyp formation. As noted earlier in greater detail, IL-1 up-regulates the expression of adhesion molecules on cultured vascular endothelium. In vivo this effect may translate into an increased traffic of lymphocytes and neutrophils into sites of inflammation. Additionally IL-1 increases T and B cell production, induces chemotaxis for neutrophils, stimulates angiogenesis and induces the production of biochemical mediators of the chronic inflammatory response such as PGE 2. These IL-1 induced pathological changes are consistent with the histopathological tissue changes observed with chronic sinusitis and polyp formation. The microscopic changes in the epithelium associated with chronic hyperplastic sinusitis and polyp formations are:

1. edema in the lamina propria;
2. infiltration of lymphocytes, neutrophiles, and plasma cells;
3. fibroblast proliferation consistent with collagen Type I production;
4. basement membrane thickening consistent with collagen IV production;
5. dilatation and compression of mucus glands consistent with polyp formation In summary, the foregoing discussion clearly establishes that one of the key controlling factors implicated and precipitating the cascade of events is Interleukin-1. IL-1 is a small peptide that is released by numerous inflammatory cells, especially macrophages. Many cells contain Interleukin-1 receptor sites. When Interleukin-1 is released and attaches to this receptor, it stimulates the proliferation of the cells and contributes to the cascade of subsequent events.

NEW METHOD OF TREATMENT

Figure 3:
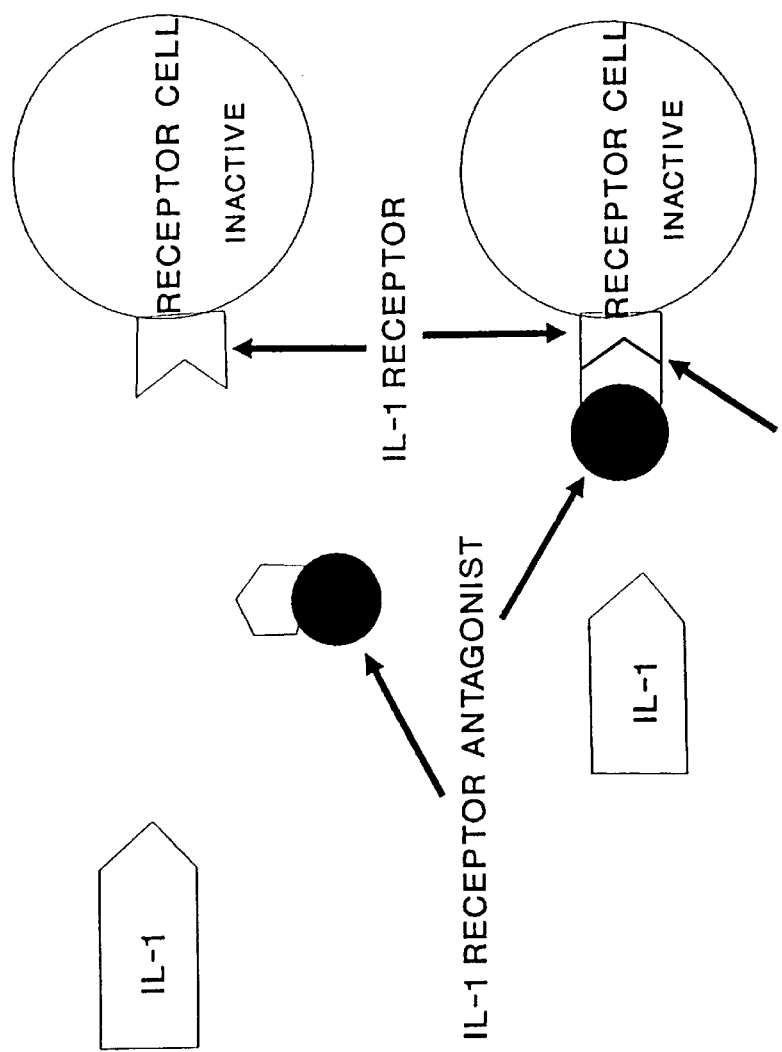
FIG. 3 is a schematic diagram showing blockage of the receptor cell activation by Interleukin-1 receptor antagonist.

It is the serendipitous discovery of the role played by interleukin-1 in the pathogenesis of obstructive, inflammatory polyps in the nose and paranasal sinuses that led the present inventors' to the discovery of the novel method of treating this disorder described hereinafter. The human body manufactures a small peptide referred to herein as IL-1 receptor antagonist which intervenes in the inflammatory response cascade. FIG. 3 describes schematically the blocking action of IL-1 receptor antagonist. The natural control over the inflammatory response cascade is exercised by means of the interleukin-1 receptor antagonist. This naturally occurring peptide is now manufactured and commercially available as Antril® (Synergen Corp.). Antril is presently undergoing clinical trials in a number of other medical applications. The IL-1 receptor antagonist binds to the interleukin-1 receptor and prevents the initiation of the cascade thereby strategically blocking the effect of interleukin-1. The IL-1 receptors are especially important on fibroblasts and T cells. Effective blockage of these IL-1 receptors can effectively intervene in a runaway inflammatory cascade.

Whereas, most of the research on interleukin has centered on tumor immunology and autoimmune areas, it is the discovery of the present inventors' that the therapeutic utilization of interleukin one antagonist (IL-1RA) can be an effective, non-toxic, treatment of this common and bothersome disorder. Current management of this disorder, as described in the prior art, is of limited efficacy and of significant expense. There are multiple medications of variable effectiveness currently on the market. Because of the chronicity of the illness, many patients are treated with medication for many years without significant resolutions with the hope of avoiding surgical intervention. In spite of persistent treatment and in spite of use of systemic and topical steroids, numerous patients will ultimately require surgical intervention. The new method of treatment provided herein intervenes in the natural inflammatory process that has gone amok, by using a natural substance that intervenes strategically with a inflammatory cascade mechanism

MODE OF DELIVERY AND TREATMENT

Introducing interleukin one receptor antagonist (IL-1RA) into the nasal polyps and paranasal sinuses, shows promising therapeutic effectiveness in dealing with this runaway disorder. While subsequent clinical trials will establish optimal dosing parameters and most compliant modes of delivery, the following discussion will be a useful guide to future research.

A preferred method of delivering the IL-1RA to a patient is through topical application in an aerosol form. In situations where greater penetration and entry into the polypoid tissue (that in some clinical situations completely obstructs the nasal cavity) is desired, commercially available delivery systems can be utilized which employ a high velocity aerosol spray injector. There are several manufactures of high velocity aerosol spray injectors, one of them being MADAJET-XL. In this injector a specific dose is introduced into a chamber and released under compression. These dosed aerosol particles have sufficient penetrating power to enter into the nasal polyps themselves in the spray form. This modality can be utilized in situations where greater penetration is required. Alternatively, an aerosol dosing bottle delivering multiple applications of IL-1RA may suffice to control or resolve this disorder. A direct injection by means of a syringe into the afflicted area or polyp can also be utilized. In the event that preferred localized site delivery of IL-1RA is difficult or lacks specific FDA approval a subcutaneous injection comprising 50–300 mg of systemic ANTRIL-® maybe utilized.

It is clear that the use of IL-1 receptor antagonist to treat sinusitis and paranasal polyps presented above is exemplary and not intended to be limiting. IL-1RA is submitted to be effective for blocking the runaway inflammatory response cascade and healing affected tissue. Many medical conditions are treatable with IL-1. In clinical management of chronic otitis media or chronic serous otitis media of childhood, an alternative mode of regional delivery may be accomplished by means of an ear drop formulation where the IL-1 receptor antagonist is delivered topically to the inflammatory tissues of the ear through the chronic perforation. Alternatively a trans tympanic injection or a limited systemic course may be considered. The present inventors submit that IL-1RA will be effective in treating this disorder and perhaps even prevent many costly operations. The clinical dosing, regional or systemic therapy will ultimately be determined by efficacy, costs, patient comfort, and FDA regulations.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What we claim is:

1. A method for effecting the localized treatment of inflamed mucosal tissue lining a cavity within the ear, nose or sinuses comprising the steps of:

(a) presenting an aerosol spray dispenser having a reservoir and a dispensing nozzle thereon, said reservoir containing a therapeutic composition comprising Interleukin-1 receptor antagonist dispersed in a pharmacologically acceptable fluid vehicle, said therapeutic composition being formulated for aerosol spray dispensation of said Interleukin-1 receptor antagonist consisting essentially of a protein having the amino acid sequence: 1

```
Met Arg Pro Ser Gly Arg Lys Ser Ser Lys
            5                   10

Met Gln Ala Phe Arg Ile Trp Asp Val Asx
                15                  20

Gln Lys Thr Phe Tyz Leu Arg Asx Asx Gln
                25                  30

Leu Val Ala Gly Tyr Leu Gln Gly Pro Asx
                35                  40

Val Asp Leu Glu Glu Lys Ile Asp Val Val
                45                  50

Pro Ile Glu Pro His Ala Leu Phe Leu Gly
                55                  60

Ile His Gly Gly Lys Met Cys Leu Ser Cys
10                  65                  70

Val Lys Ser Gly Asp Glu Thr Arg Leu Gln
                75                  80

Leu Glu Ala Val Asp Ile Thr Asp Leu Ser
                85                  90

Glu Asp Arg Lys Gln Asp Lys Arg Phe Ala
                95                  100

Phe Ile Arg Ser Asp Ser Gly Pro Thr Thr
                105                 110

Ser Phe Glu Ser Ala Ala Cys Pro Gly Trp
                115                 120

Phe Leu Cys Thr Ala Met Glu Ala Asp Gln
                125                 130

Pro Val Ser Leu Thr Asp Met Pro Asp Glu
                135                 140

Gly Val Met Val Thr Lys Phe Tyr Phe Glx
                145                 150

Glu Asp Glu;
```

(b) placing the dispensing nozzle in fluid communication with the cavity; and (c) spraying the therapeutic composition into the cavity until at least a portion of the therapeutic composition impinges upon said inflamed mucosal tissue.

* * * * *

SEQUENCE LISTING (1) GENERAL INFORMATION:

(iii) NUMBER OF SEQUENCES:1

(2) INFORMATION FOR SEQ ID NO:1:

(i) SEQUENCE CHARACTERISTICS:
      (A) LENGTH:153
      (B) TYPE:Amino Acid
      (C) TOPOLOGY:Unknown (ii) MOLECULE TYPE:Protein (iii) HYPOTHETICAL:No (iv) ANTI-SENSE:No (v) FRAGMENT TYPE:Internal Fragment Recombinant DNA (vi) ORIGINAL SOURCE:
      (A) ORGANISM:Unknown
      (B) STRAIN:Unknown
      (C) INDIVIDUAL ISOLATE:Unknown
      (D) DEVELOPMENTAL STAGE:Unknown
      (E) HAPLOTYPE:Unknown
      (F) TISSUE TYPE:Unknown
      (G) CELL TYPE:Unknown
      (H) CELL LINE:Unknown
      (I) ORGANELLE:Unknown (vii) IMMEDIATE SOURCE:
      (A) LIBRARY:N/A
      (B) CLONE:N/A (viii) POSITION IN GENOME:
      (A) CHROMOSOME/SEGMENT: Unknown
      (B) MAP POSITION:Unknown
      (C) UNITS:Unknown (ix) FEATURE:
      (A) NAME/KEY:N/A
      (B) LOCATION:N/A
      (C) IDENTIFICATION METHOD:  N/A
      (D) OTHER INFORMATION:Commercially available, Interleuken-I
         Receptor Antagonist sold by Sy (x) PUBLICATION INFORMATION:
      (A) AUTHORS:Hannum, Charles H.
         Eisenberg, Robert C.
         Arend, William P.
         Joslin, Fenneke G.
      (B) TITLE:INTERLEUKIN I INHIBITORS
      (C) JOURNAL:US Patent
      (D) VOLUME:N/A
      (E) ISSUE:N/A
      (F) PAGES:N/A
      (G) DATE:N/A
      (H) DOCUMENT NUMBER:5,075,222
      (I) FILING DATE:06 APR 1990
      (J) PUBLICATION DATE:24 DEC 1991
      (K) RELEVANT RESIDUES IN SEQ ID NO:N/A (xi) SEQUENCE DESCRIPTION: SEQ ID NO:1:

-continued

```
Met Arg Pro Ser Gly Arg Lys Ser Ser Lys Met Gln Ala
            5                   10

Phe Arg Ile Trp Asp Val Asx Gln Lys Thr Phe Tyr Leu
    15                  20              25

Arg Asx Asx Gln Leu Val Ala Gly Tyr Leu Gln Gly Pro
            30                  35

Asx Val Asp Leu Glu Glu Lys Ile Asp Val Val Pro Ile
40                  45                  50

Glu Pro His Ala Leu Phe Leu Gly Ile His Gly Gly Lys
            55              60                  65

Met Cys Leu Ser Cys Val Lys Ser Gly Asp Glu Thr Arg
                70                  75

Leu Gln Leu Glu Ala Val Asp Ile Thr Asp Leu Ser Glu
80                  85                  90

Asp Arg Lys Gln Asp Lys Arg Phe Ala Phe Ile Arg Ser
            95                  100

Asp Ser Gly Pro Thr Thr Ser Phe Glu Ser Ala Ala Cys
105             110                 115

Pro Gly Trp Phe Leu Cys Thr Ala Met Glu Ala Asp Gln
    120                 125                     130

Pro Val Ser Leu Thr Asp Met Pro Asp Glu Gly Val Met
                135             140

Val Thr Lys Phe Tyr Phe Glx Glu Asp Glu
    145                 150
```